United States Patent
Solomon et al.

(10) Patent No.: US 7,325,465 B2
(45) Date of Patent: Feb. 5, 2008

(54) PARTICLE MATTER SAMPLING METHOD AND SAMPLER WITH A VIRTUAL IMPACTOR PARTICLE CONCENTRATOR

(75) Inventors: Paul A. Solomon, Henderson, NV (US); Constantinos Sioutas, Pasadena, CA (US)

(73) Assignee: U.S. Environmental Protection Agency, Washington, DC (US)

( * ) Notice: Subject to any disclaimer, the term of this patent is extended or adjusted under 35 U.S.C. 154(b) by 158 days.

(21) Appl. No.: 11/049,303

(22) Filed: Feb. 3, 2005

(65) Prior Publication Data

US 2006/0169065 A1    Aug. 3, 2006

(51) Int. Cl.
    *G01N 1/22* (2006.01)
(52) U.S. Cl. .................................. 73/863.22
(58) Field of Classification Search ............. 73/863.22, 73/863.23; 209/133, 138, 143
    See application file for complete search history.

(56) References Cited

U.S. PATENT DOCUMENTS

| | | | | |
|---|---|---|---|---|
| 4,301,002 A | * | 11/1981 | Loo ........................... | 209/143 |
| 4,767,524 A | * | 8/1988 | Yeh et al. .................... | 209/143 |
| 5,040,424 A | * | 8/1991 | Marple et al. ............ | 73/863.23 |
| 2006/0162424 A1 | * | 7/2006 | Shekarriz et al. .......... | 73/28.06 |

* cited by examiner

*Primary Examiner*—Hezron Williams
*Assistant Examiner*—Tamiko Bellamy
(74) *Attorney, Agent, or Firm*—Bacon & Thomas, PLLC; George A. Loud, Esq.

(57) ABSTRACT

An apparatus for sampling ambient air to obtain coarse and fine fractions of particulate matter includes a single acceleration tube and a collection tube coaxially arranged along a central axis with a gap between facing distal ends thereof within a range of d/D1 of 1 to 2, wherein d is the distance or gap between the distal ends and D1 is the inside diameter of the outlet at the distal end of the acceleration tube. A housing surrounding the acceleration and concentration tubes is provided with a side-wall nozzle connected to a suction device for drawing a major portion of the sampled ambient air therethrough and for separation of particulate matter, as a fine fraction, from that major portion. A second suction device draws a minor portion of the sampled ambient air, containing the coarse fraction of the particulate matter, in a straight path approximating the central axis, through the acceleration tube and through the collection tube for passage through a filter for separation of the coarse fraction of particulate matter. The ratio of the flow rates of the major and minor portions of the sampled ambient air is adjusted to provide a cutpoint within the range of 2-3 microns. The apparatus is preferably operated with a flow rate for the sampled ambient air within the range of 900-1200 liters per minute.

17 Claims, 7 Drawing Sheets

PARTICLE MATTER SAMPLING METHOD AND SAMPLER WITH A VIRTUAL IMPACTOR PARTICLE CONCENTRATOR

BACKGROUND OF THE INVENTION

1. Field of the Invention

The present invention is directed to the sampling of ambient air and separation and collection of particulate matter fractions (PM) from the sample.

2. The Related Art

Airborne particulate matter, known as PM, is one of the major components of smog. PM includes microscopic particles in the air that are divided into two size ranges: PM2.5 and PM 10. PM2.5 refers to "fine" particles less than 2.5 micrometers (microns) in size about 1/20th the width of a human hair. Likewise, PM10 refers to particles less than 10 microns in size. As used herein, "coarse" has reference to a PM fraction 2.5-10 microns in size.

PM can be released directly to the atmosphere from such sources as industrial smokestacks, automobile tailpipes, wood burning and road dust, to mention a few. PM can also form in the atmosphere from chemical reactions involving other pollutants such as sulphur dioxide ($SO_2$), nitrogen oxides ($NO_X$), ammonia ($NH_3$), and volatile organic compounds (VOC).

According to a New Scientist article (Inside Science, No. 84, 1995) large particles are filtered out by the nose. Middle size particles deposited in the airways are trapped on a layer of mucus which sweeps them to the throat, where they are coughed up or swallowed. Only particles less than 2 microns reach the alveoli, where they must be dealt with by macrophages from the immune system. Particles less than 2 microns in size can be inhaled deep into the lungs and reach the critical areas where the cells replenish the blood with oxygen. They can cause breathing and respiratory symptoms, irritation, inflammation and damage to the lungs. Health studies have shown significant associations between exposure to PM2.5 and premature death from heart or lung disease. Fine particles (PM2.5) also aggravate heart and lung diseases and have been linked to effects such as cardiovascular symptoms, cardiac arrhythmias, congestive heart failure, heart attacks, respiratory symptoms, asthma attacks, and bronchitis. These effects can result in increased hospital admissions, emergency room visits, absences from school or work, and restricted activity days. Individuals that may be particularly sensitive to PM2.5 exposure include people with heart or lung disease, older adults and children.

Accordingly, the U.S.E.P.A. has published rules setting forth air quality designations and classifications for fine particulates (PM2.5) pursuant to the National Ambient Air Quality Standards (NAAQS).

Despite the growing evidence of particulate-related health effects, the paucity of information about specific biological mechanisms remains a critical missing link.

In addition to PM2.5, coarse PM (2.5-10 µm in aerodynamic diameter) may also consist of several potentially toxic components, such as resuspended particulate matter from paved and unpaved roads, industrial materials, brake linings, tire residues, trace metals, and bioaerosols. A considerable fraction of these particles may deposit in the upper airways and to a lesser extent into the lower airways, and may be responsible for the exacerbation of asthma. Recent data from a small number of epidemiological studies indicate that, apart from—or in addition to—the fine PM fraction, health effects may also be closely associated with the coarse PM fraction and sometimes even to a larger extent (Ostro et al., 1999, Kleinman et al., 2000) than PM2.5. In vitro studies with human monocytes (Monn and Becker, 1998; Becker et al., 1996) show that cellular toxicity and inflammation may also be associated with the coarse fraction (2.5-10 µm) and its biological components. Also, in vitro data from Romberg et at. (1998a,b) on genotoxicity of ambient fine and coarse mode PM collected from an urban area characterized by a high traffic density suggests that coarse mode PM may have comparable or even higher activity. Collectively, these studies indicated that the coarse mode PM might still contribute to a certain extent to observed health effects, especially those occurring in the higher airways like asthma.

Accordingly, a need exists for sampling ambient air, and separating particulates therefrom as coarse and fine fractions separated by a sharp cut point at 2.5 microns.

SUMMARY OF THE INVENTION

Accordingly, the present invention provides an apparatus for sampling ambient air and removing particulate matter from the sampled ambient air as separate coarse and fine fractions. The apparatus of the present invention includes a single acceleration tube extending along a central axis and comprising a conical section tapering from the sample receiving end down to an outlet straight cylinder section integral therewith. The outlet straight cylinder section has a constant diameter D1 and extends from the conical section to an outlet at a first distal end. The apparatus of the present invention further includes a collection tube comprising an inlet straight cylinder section axially aligned with the acceleration tube, having a constant diameter D2 and extending along the central axis from an inlet at a second distal end to a conical section integral therewith. The conical section of the collection tube tapers from the diameter D2 to a discharge end of a diameter D3 larger than diameter D2. The ratio of D2/D1 is: >1 to 2. The first and second distal ends face each other and are spaced apart by a distance d, wherein the ratio of d/D1 is 1 to 2. The apparatus further includes a housing surrounding at least the outlet straight cylinder section of the acceleration tube and the inlet straight cylinder section of the collection tube and has a nozzle in a side-wall which extends along a nozzle axis. In a preferred embodiment the nozzle axis intersects the central axis at an angle of approximately 90°.

The sampled ambient air enters the sample receiving end of the acceleration tube at a first flow rate FR1 and a major portion thereof, containing the PM fine fraction, is drawn through the side-wall nozzle by a large volume suction device at a second flow rate FR2. A minor portion of the sampled ambient air, containing the PM coarse fraction, is drawn through the collection tube by a small volume suction device at a third flow rate of FR3. The major and minor portions of the sampled ambient air are passed through separate particulate collectors for collection of the fine and coarse fractions, respectively.

The purpose of providing desired cuts of the particulate matter contained in the sampled ambient air, the apparatus of the present invention preferably further includes a conventional particulate matter, high volume air sampler ("separating device") for separating particulates larger than the coarse fraction and delivering the ambient air containing the coarse and fine fractions to the sample receiving end of the acceleration tube. In order to evaluate attainment of current standards of the U.S.E.P.A. for particulate matter, the separating device connected to the upstream side of the acceleration tube should remove particulate matter larger than PM10 (10 microns in aerodynamic diameter) and at least one of the flow rates FR2 and FR3 should be adjusted to a ratio of FR2/FR3 providing a sharp cutpoint between the coarse and fine fractions within the range of 2-3 microns, preferably, approximately PM2.5. For this purpose, the ratio of FR2/FR3 is in the range of 8:1 to 30:1, preferably approximately 25:1.

In the acceleration tube, the conical section should join the inlet and outlet straight cylinder sections at an angle of 45° or less in order to minimize air turbulence and obtain a finer cut between fine and coarse fractions.

The cutpoint between the fine and coarse fractions should be within the range of 2.0-3.0 in order to provide a sharp cutpoint. Further, particles coarser than about 2.5 microns tend to be basic whereas finer particles tend to be acidic. Accordingly, a cutpoint larger than about 2.5 microns tends to collect both acidic and basic particles and consequently, the mixture becomes less representative of atmospheric chemistry.

The method of the present invention includes introducing ambient air containing particulate matter into the sample receiving end of the accelerator tube and drawing a major (first) portion of the introduced ambient air containing the PM fine fraction at a second flow rate FR2, through the side-wall nozzle. The method further includes drawing a minor (second) portion of the introduced ambient air, containing the PM coarse fraction, through the collection tube at a third flow rate FR3. The method also involves separating the PM fine fraction from the major portion of the introduced ambient air and separating the PM coarse fraction from the minor portion of the introduced ambient air.

As indicated above, the preferred method would also involve removing particulate matter larger than about 10 microns from the sampled ambient air prior to introduction of the ambient air into the sample receiving end of the acceleration tube. Preferably, the method further comprises adjusting at least one of the flow rates FR2 and FR3 to obtain a separation of fine and coarse fractions at a cutpoint within the range of 2-3 microns, preferably approximately 2.5 microns. As noted above, for this purpose, the ratio of FR2/FR3 would be adjusted to a value within the range of 8:1 to 30:1, preferably 25:1.

In the method of the present invention the flow rate of the sampled ambient air introduced into the sample receiving end of the acceleration tube (FR1) is preferably within the range of 900-1200 liters per minute. The flow rate of the major portion of the ambient air diverted through the side-wall nozzle is preferably 800-1160 liters per minute and the flow rate of the minor portion of the sampled ambient air is preferably 40-100 liters per minute at the inlet end of the collection tube.

DESCRIPTION OF THE PREFERRED EMBODIMENTS

Preferred embodiments of the invention will now be described with reference to the accompanying drawings. As used herein "flow rate" means volumetric flow rate. Particle size, expressed in microns, should be understood as aerodynamic diameter, as conventionally used in the art.

Figure 1:
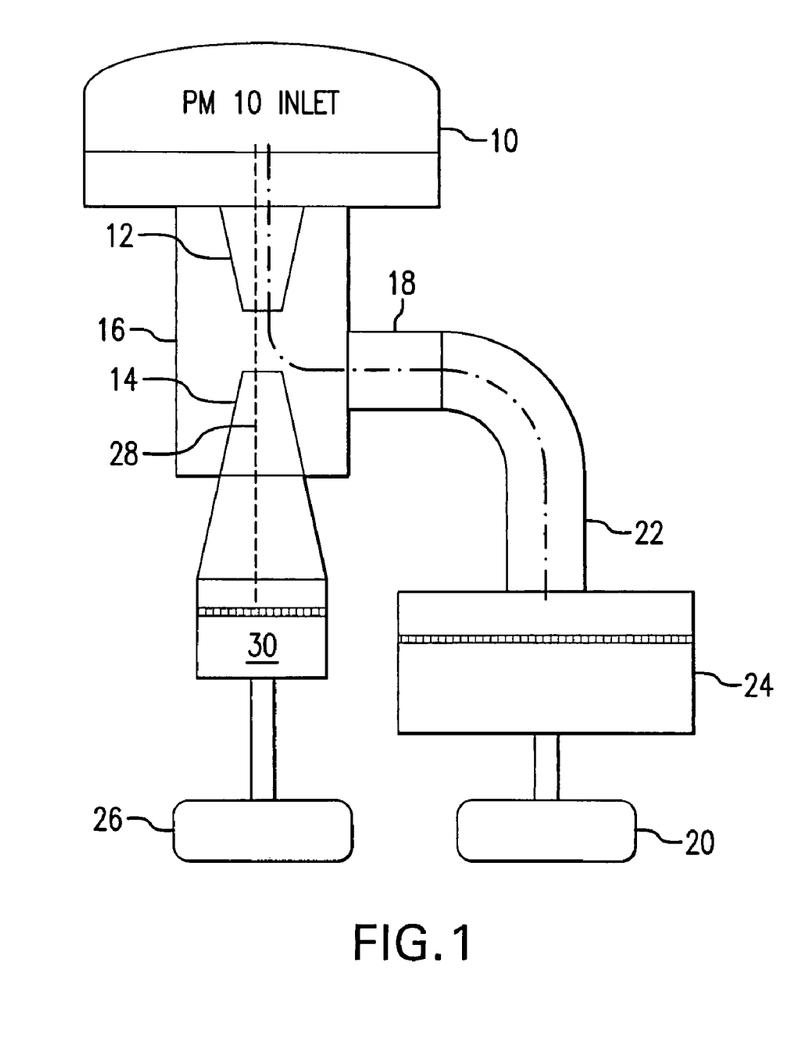
FIG. 1 is a schematic view of the apparatus of the present invention.

FIG. 1 shows a preferred embodiment as including a PM10 separating device 10, an acceleration tube 12, a collection tube 14 and a housing 16 surrounding the acceleration tube 12 and collection tube 14. The housing 16 has a side-wall nozzle 18 through which a major portion of the sampled ambient air is drawn by a large volume suction device, e.g., the suction side of an air pump 20 with volumetric flow control. The fine particle cut 22, i.e., 2-3 microns and smaller, is separated and collected in a fine particulate collector, e.g., filter and filter holder 24. A small volume suction device, e.g., the inlet side of air pump 26 with volumetric flow control, draws a minor portion of the sampled ambient air, containing coarse fraction 28 of the particulate matter, through the collection nozzle 14, whereby the coarse fraction 28 is separated and collected by a coarse particulate collector, e.g., filter and filter housing 30.

The separating device 10 is preferably a high volume PM10 which removes particulates larger than 10 microns, such as one of models TE-6070, TE-6070D, TE-6070V and TE-6070DV marketed by Tisch Environmental, Inc.

Figure 2:
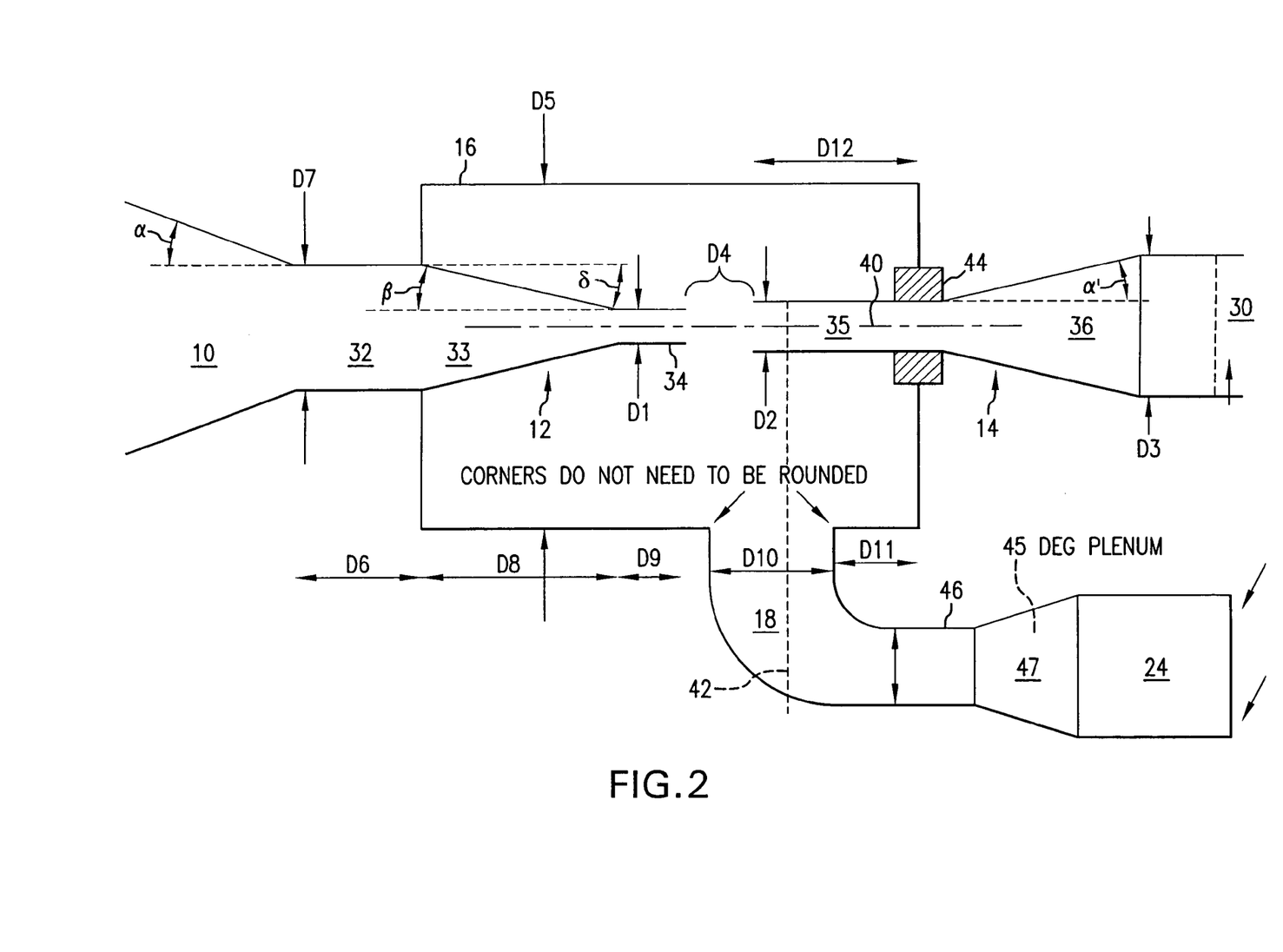
FIG. 2 is another schematic view of the apparatus of the present invention showing various design features in greater detail.
Figure 3:
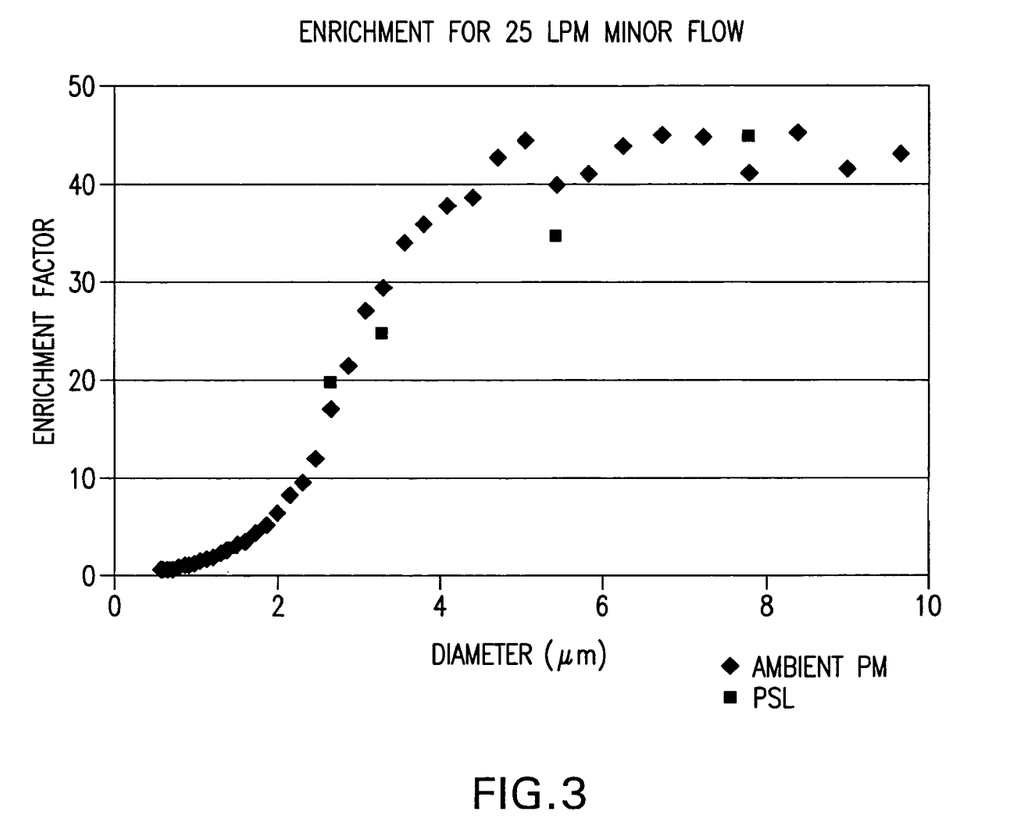
FIG. 3 is a graph showing enrichment in concentration of particulate matter in air obtained by passage through the apparatus of the present invention as shown in FIGS. 1 and 2, operated with a flow rate for the minor portion of 25 liters per minute.
Figure 4:
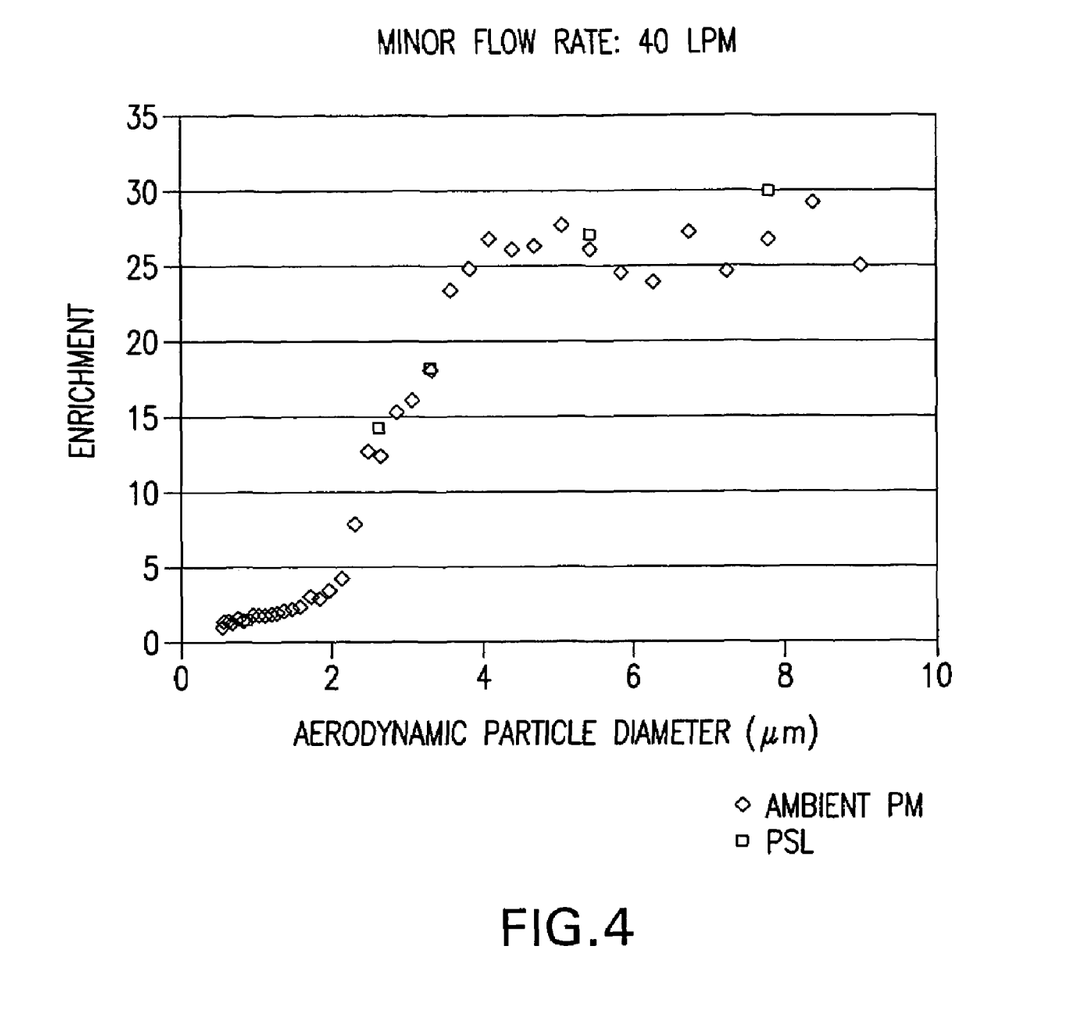
FIG. 4 is a graph similar to FIG. 3 but with a flow rate of 40 liters per minute for the minor portion.

FIG. 2 shows design details, inclusive of features important in the context of the intended manner of operation. As seen in FIG. 2, the acceleration tube 12 includes an inlet straight cylinder section 32 of constant inside diameter D7, a conical section 33, and an outlet straight cylinder section 34 of constant inside diameter D1, all integrally joined. The inlet straight cylinder section 32 connects to the Tisch PM10 separating device 10 at an angle α and connects to the conical section 33 at an angle δ. The conical section 33 connects at its downstream (smaller) end to the outlet straight cylinder section 34 at an angle β. Angles α, β and δ are preferably 45° or less, more preferably 20-45°, to minimize turbulence and thereby provide a more precise cut point, preferably at PM2.5, to better enable determination of compliance with the aforementioned U.S.E.P.A. standard.

The collection tube 14 includes an inlet straight cylinder section 35 with a constant inside diameter (I.D.) D2, and joined thereto at an angle $α^1$, a conical section 36. The conical section 36 tapers from I.D. D2 to I.D. D3 where it is joined to a coarse particulate collector, which in the embodiment depicted in FIGS. 1 and 2 is shown as filter 30. As shown in FIG. 2 the collection tube 35 is axially-aligned with the acceleration tube 33, along a central axis 40. The angle $α^1$ is not critical but is suitably 20-45°, preferably approximately 45°.

While the particulate collectors 24 and 30 have been described as filters, any suitable conventional collector, e.g., an electroprecipitator, could be used.

Experimental

The experiments described here employed a PM10 inlet commercially available from Tisch (PM10 Hi-Vol Sampler, Tisch Environmental, Cleaveland, Ohio), followed by a single round nozzle virtual impactor in the form of an acceleration tube 12 axially aligned with a collection tube 14 as shown in FIG. 2. The virtual impactor was operated with an intake flow rate of 1000 liters/minute (LPM). Particles smaller than 10 μm in aerodynamic diameter were drawn through the virtual impactor and accelerated in passage through acceleration tube 12, which was designed to have a theoretical 50% cut point at about 2.5 μm for an intake flow rate of 1000 LPM. The acceleration nozzle jet was 1.4 cm in diameter (I.D.)(D1=1.4 cm), whereas the collection nozzle was 2 cm in I.D. (D2=2 cm). The two nozzles were separated by a gap of 2 cm (D4).

The diameter of the cylindrical housing 16 (D5) was 10 cm. The straight cylinder inlet section 32 had an I.D. (D7) of 5 cm and a length (D6) of 5 cm (D6 can be up to 20 cm). The conical section 33 had a length D8 of 4.5 cm and the outlet straight cylinder section 34 had a length D9 of 1.5 cm. The side-wall nozzle 18 had an I.D. (D10) of 5 cm and was aligned on a nozzle axis 42 intersecting central axis 40 at an angle of approximately 90°. Side-wall nozzle 18 was connected to an inlet 46 (I.D. 5 cm) and 45° plenum 47 of filter housing 24. D11 was 1.5 cm.

For the collection tube 14 the inlet straight cylinder section extended 5 cm from support 44 (D12=5 cm) and the conical section 36 extended therefrom at a 45° angle to join to the inlet side of filter housing 30.

The 50% cut point can be estimated from the Stokes number, St, defined as (Hinds, 1999):

$$St = \frac{\rho_p U_i d_p^2 C_c}{9\mu d_0} \quad (1)$$

where $d_p$, $\rho_p$, $C_c$ are the particle diameter, density and slip correction, μ is the air viscosity ($1.81 \times 10^{-4}$ g/cm·sec), $U_i$ is the velocity through the acceleration jet, and $d_0$ is the inside diameter of the acceleration nozzle ($d_0$=D1=1.4 cm). The St corresponding to 10 μm particles is 0.30, based on the nozzle dimensions and the flow rate, which is close to the value typically corresponding to the 50% cut point of round-nozzle impactors (Marple and Liu, 1974).

Coarse-mode particles (2.5-10 μm) travel in an approximately straight path (28 in FIG. 1) due to their inertia, cross the deflected air streamlines (22 in FIG. 1) and are drawn through the collection nozzle 18 (minor flow). Particles smaller than the cut point of the virtual impactor (here 2.5μ) are diverted along the major flow path 28. The minor flow rate can vary from 3-10% of the intake flow rate, depending on desired exposure concentration level and/or exposure flow rate needed. The pressure drop across the major flow path of the virtual impactor was 40 inches H₂O.

The performance of the apparatus shown in FIGS. 1 and 2 and its components were tested using a variety of different technologies and ambient aerosols. Several continuous and semi-continuous particle measurement instruments were used to measure aerosol characteristics before and after enrichment. First, concentration enrichment as a function of particle size was determined by measuring the concentrations upstream and downstream of the virtual impactor by means of the TSI Aerodynamic Particle Sizer (APS TSI Model 3320). Tests were conducted at minor flow rates of and 25 and 40 LPM, and the concentration enrichment factors, plotted in FIGS. 3 and 4, were based on averages of repeated tests. For each configuration, at least 10 measurements upstream and downstream of the virtual impactor were taken.

Following the APS characterization, the sampler was evaluated in collocation with a modified Micro-Orifice Uniform Deposit Impactor (MOUDI, MSP Corporation, Minneapolis, Minn.) and a R&P Partisol Dichotomous Sampler at the facilities of the University of Southern California, in downtown Los Angeles In the field tests, the coarse speciation sampler operated at a total flow rate of 1,000 LPM and with a minor flow rate adjusted to 100 LPM. The ideal enrichment factor corresponding to this minor-to-total flow ratio would thus be 10.

The 100 LPM of minor flow were drawn into 90 mm filters 30 (2 μm, PTFE, Gelman, Ann Arbor, Mich.) whereas the 900 LPM of the major flow were drawn through 8×10 Teflon coated glass fibre filters 24 (2 μm, PTFE, Gelman, Ann Arbor, Mich.). The MOUDI sampled at 30 LPM and was modified (from its original 8-stage configuration) to include only 2 stages, collecting size-segregated particles in aerodynamic diameter ranges of 0-2.5 and 2.5-10, respectively. 4.7 cm PTFE filters were used as impaction substrates in coarse PM MOUDI stages. The Partisol sampled at 16.7 LPM total flow, of which 1.67 LPM and 15 LPM were diverted into 47 mm Teflon filters for the minor and major flow collections, respectively.

Particle mass, sulfate, nitrate concentrations, as well as concentrations of trace elements and metals were determined for both ambient and concentrated aerosols measured by the three samplers. Only mass measurements were conducted for the MOUDI, whereas mass, inorganic on and trace element concentrations were determined for both the coarse PM speciation sampler and the Partisol. The sampling periods varied from 3 to 12 hours depending on the observed PM level. To determine particle mass concentrations, the PTFE filters of the MOUDI, Partisol and Tisch samplers were pre-weighed and post-weighed using a Microbalance (MT 5, Mettler-Toledo Inc., Highstown, N.J.; Sartorius microbalance MC-5, Sartorius AG, Goettingen, Germany) in a room with controlled temperature of 21-24° C. and relative humidity of 40-50%. Filters were weighed twice in order to increase precision. In case of a difference of more than 3 μg between consecutive weighings, the filter was weighed a third time or reweighed until two consecutive weighings differed by less than 3 μg.

Fifteen out of 21 pairs of PTFE filter samples collected by the Tisch and Partisol samplers were then analyzed by means of x-ray fluorescence (XRF) to determine concentrations of selected elements and metals. The remaining 6 pairs of coarse, as well as fine PM samples, were extracted with 0.15 ml of ethanol and 5 ml of ultrapure water. Ethanol was used in order to wet the hydrophobic Teflon filter. The samples were sonicated for 15 minutes and analyzed for sulfate and nitrate ions by means of ion chromatography (IC). Samples that were lower than three times the lower limits of detection (LaD) of either XRF or IC were excluded.

Coarse PM mass concentration data determined by Tisch, MOUDI and Partisol are shown in Table 1. In all subsequent tables and figures, the coarse particle concentration are in $\mu g/m^3$ and have been normalized to the intake flows of the Tisch, MOUD I and Partisol samplers, i.e., at 1000, 30 and 16.7 LPM, and not to the minor flows of the virtual impactors for the Tisch and Partisol.

TABLE 1

Coarse PM Concentrations Measured
by the Tisch, MOUDI and Partisol

| Sample No | Tisch | MOUDI | Partisol | TISCH/ MOUDI | Tisch/ Partisol | TISCH/ AVG MOUDI-Partisol |
|---|---|---|---|---|---|---|
| 1 | 19.73 | 19.63 | 18.40 | 1.00 | 1.07 | 1.04 |
| 2 | 13.49 | 14.58 | 14.32 | 0.93 | 0.94 | 0.93 |
| 3 | 18.06 | 19.38 | 20.05 | 0.93 | 0.90 | 0.92 |
| 4 | 17.84 | 18.30 | 19.40 | 0.98 | 0.92 | 0.95 |
| 5 | 12.18 | 14.81 | 12.64 | 0.82 | 0.96 | 0.89 |
| 6 | 10.44 | 12.06 | 11.08 | 0.87 | 0.94 | 0.90 |
| 7 | 22.82 | 24.88 | 29.06 | 0.92 | 0.79 | 0.85 |
| 8 | 23.14 | 27.16 | 24.57 | 0.85 | 0.94 | 0.89 |
| 9 | 22.19 | 27.04 | 21.84 | 0.82 | 1.02 | 0.91 |
| 10 | 13.60 | 16.11 | | 0.84 | | 0.84 |
| 11 | 10.44 | 12.59 | 12.54 | 0.83 | 0.83 | 0.83 |
| Average | | | | 0.89 | 0.93 | 0.90 |
| SD | | | | 0.06 | 0.08 | 0.06 |

Very good overall agreement can be seen among the three samplers, with the somewhat lower concentrations measured by Tisch (by roughly 10%) being probably due to cutpoint differences between its virtual impactors and those of the MOUDI and Partisol.

Figure 5:
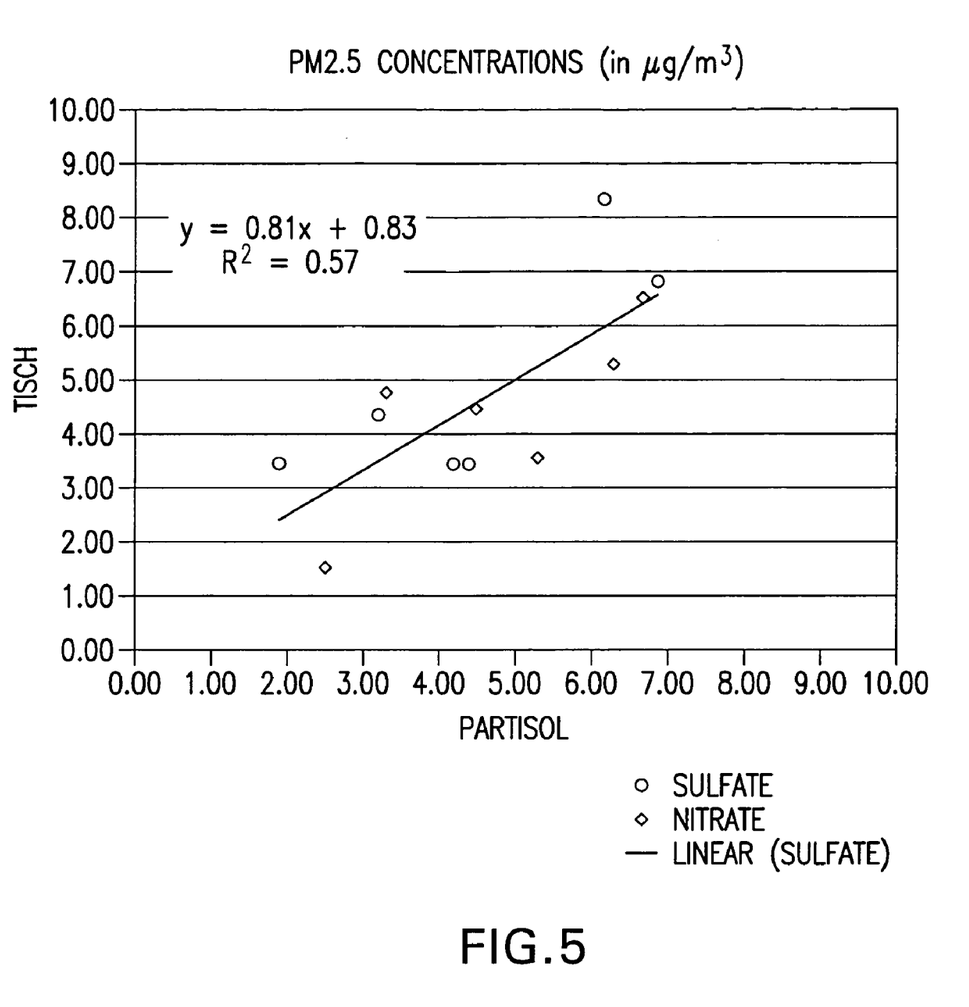
FIG. 5 is a graph for PM2.5 concentrations obtained in comparative testing.
Figure 6:
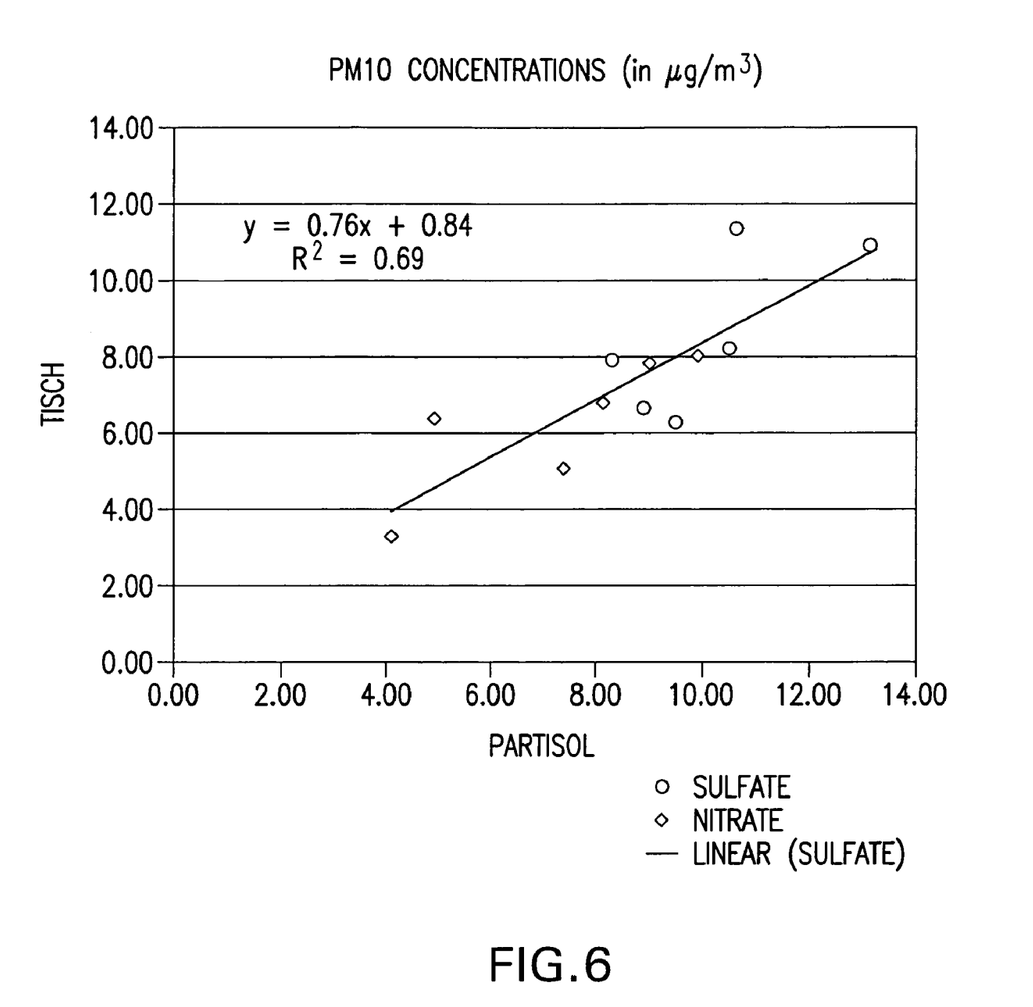
FIG. 6 is a graph of PM10 concentrations obtained in comparative testing.

The results of comparing coarse particulate nitrate and sulfate concentrations collected by the Tisch and Partisol are shown in FIGS. 5 and 6 and Tables 2-3.

TABLE 2

Nitrate Concentrations

| Coarse Partisol | Tisch | Fine Partisol | Tisch | Ratio Coarse | PM10 Partisol | Tisch | Ratio Fine | Ratio PM10 |
|---|---|---|---|---|---|---|---|---|
| 6.30 | 4.90 | 4.20 | 3.40 | 0.78 | 10.50 | 8.30 | 0.81 | 0.79 |
| 5.10 | 3.70 | 3.20 | 4.30 | 0.73 | 8.30 | 8.00 | 1.34 | 0.96 |
| 5.10 | 2.90 | 4.40 | 3.40 | 0.57 | 9.50 | 6.30 | 0.77 | 0.66 |
| 4.40 | 3.20 | 6.20 | 8.20 | 0.73 | 10.60 | 11.40 | 1.32 | 1.08 |
| 6.20 | 4.20 | 6.90 | 6.70 | 0.68 | 13.10 | 10.90 | 0.97 | 0.83 |
| 7.00 | 3.30 | 1.90 | 3.40 | 0.47 | 8.90 | 6.70 | 1.79 | 0.75 |
| Average | | | | 0.66 | | | 1.17 | 0.85 |
| SD | | | | 0.12 | | | 0.39 | 0.15 |

TABLE 3

Sulfate Concentrations

| Coarse Partisol | Tisch | Fine Partisol | Tisch | Ratio Coarse | PM10 Partisol | Tisch | Ratio Fine | Ratio PM10 |
|---|---|---|---|---|---|---|---|---|
| 1.60 | 1.80 | 2.50 | 1.50 | 1.13 | 4.10 | 3.30 | 0.60 | 0.80 |
| 1.60 | 1.70 | 3.30 | 4.70 | 1.06 | 4.90 | 6.40 | 1.42 | 1.31 |
| 2.10 | 1.60 | 5.30 | 3.50 | 0.76 | 7.40 | 5.10 | 0.66 | 0.69 |
| 3.60 | 2.90 | 6.30 | 5.20 | 0.81 | 9.90 | 8.10 | 0.83 | 0.82 |
| 2.30 | 1.50 | 6.70 | 6.40 | 0.65 | 9.00 | 7.90 | 0.96 | 0.88 |
| 3.60 | 2.50 | 4.50 | 4.40 | 0.69 | 8.10 | 6.90 | 0.98 | 0.85 |
| Average | | | | 0.85 | | | 0.91 | 0.89 |
| SD | | | | 0.20 | | | 0.30 | 0.21 |

The sulphate-based concentrations for both PM2.5 and coarse PM agree quite well, with the slightly smaller coarse PM measured by the Tisch again being due to cutpoint differences, as sulfate and nitrate in Los Angeles have a significant mass fraction (i.e., 30-40%) in the 1-3 μm range (Geller et al. 2004). Hence, a small cutpoint difference may result in substantial differences in the concentrations measured by the 2 samplers. The PM10 concentrations also agree well between the two samplers, whereas for nitrate the coarse concentrations measured by the Tisch appear to be smaller by about 30%. The higher PM2.5 nitrate concentrations and the overall good agreement based on PM10 nitrate suggest that some of that difference may be due to cutpoint differences. However, it is likely that some of it may be related to higher losses of nitrate by volatilization in the Tisch sampler. This is because the filter face velocity in the coarse PM collector of the Tisch sampler is more than one order of magnitude higher compared to that of the Partisol.

Figure 7:
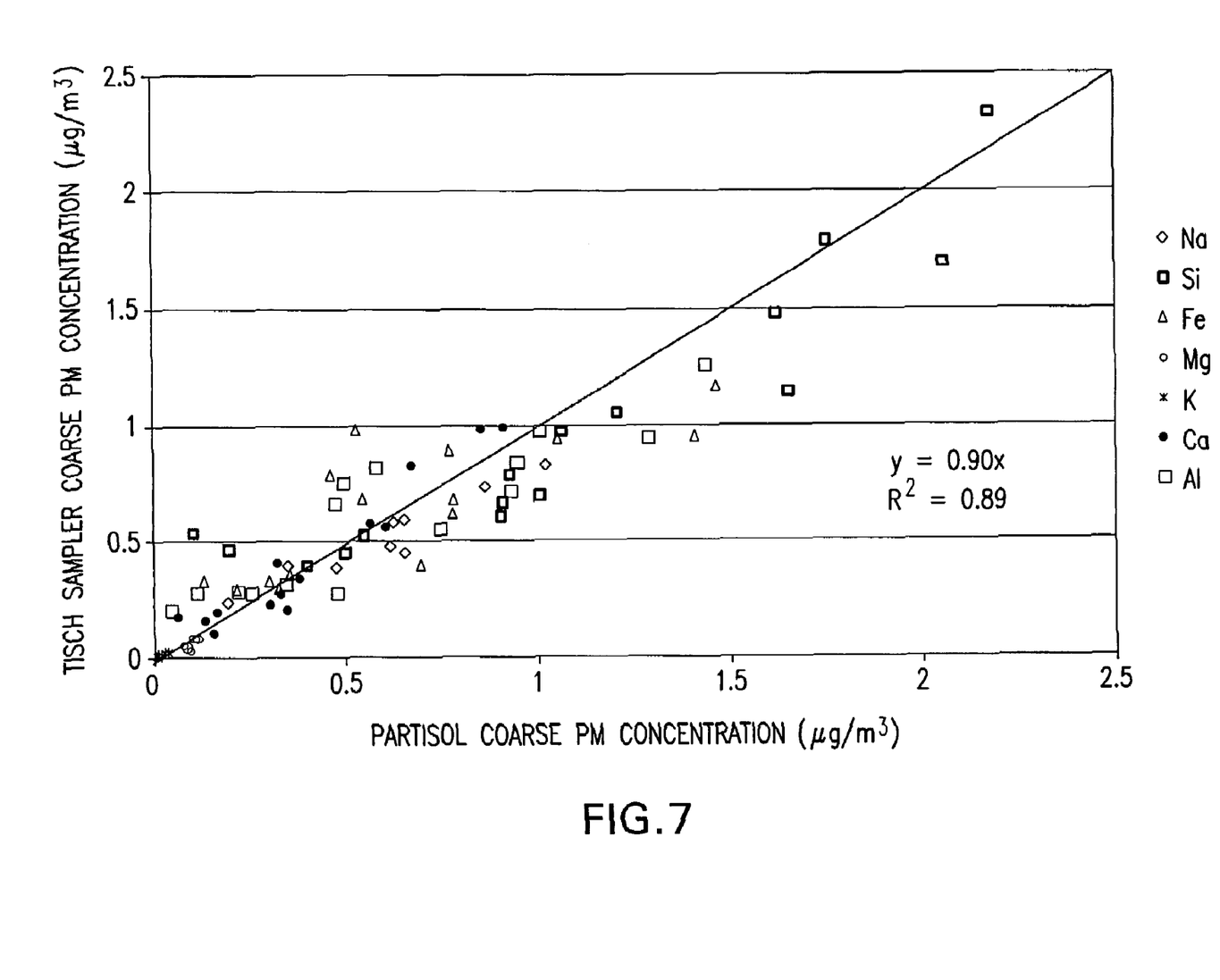
FIG. 7 is a graph for coarse particulate matter concentrations obtained in comparative testing.

The Tisch and Partisol comparison based on coarse PM concentrations of trace elements and metals is shown in FIG. 7 and summarized in Table 4. The following metals and elements were selected based on their relative high amounts in the coarse mode relative to the fine mode PM: Al, Si, Ca, K, Fe, Cu, and Na. Other elements were detected in the Tisch but not the Partisol sampler, given its much lower sampling flow rate, thus comparisons cannot be made for these elements based on insufficient data points. As in the previous cases where we report mass, sulfate and nitrate concentrations, the coarse PM concentrations of Tisch and Partisol are normalized to the intake flow of the samplers and not to the minor flows.

The much higher (i.e., close to 1) Tisch-Partisol ratios obtained for the seven trace elements and metals indicate an overall excellent agreement between the two samplers for coarse PM. The overall correlation coefficient between the Tisch-Partisol data was $R^2=0.89$ as shown in FIG. 7, thereby indicating a high degree of correlation between the trace element and metal concentrations obtained with these two samplers. The much better agreement observed for these species compared to coarse PM nitrate (and to a lesser extent sulfate) is very likely due to the larger size distribution of these metals within the coarse mode compared to nitrate and sulphate. In that case, small differences in the cutpoints of the Tisch and Partisol virtual impactors would not result in substantial difference in the coarse mode measurements of species that are partitioned in sizes that are appreciably larger (i.e., >3 μm) than the cutpoints of the two samplers. The fact that these elements are also non-labile species, thus not prone to sampling artifacts related to losses of volatile compounds, further contributes to better agreement between Tisch and Partisol.

TABLE 4

Coarse PM Concentrations of Trace Element and Metals Obtained by Means of the Tisch and Partisol Samplers

| | Na | | Si | | Fe | | K | | Al | | Ca | | Cu | |
|---|---|---|---|---|---|---|---|---|---|---|---|---|---|---|
| | Partisol | Tisch | Partisol | Tisch | Partisol | Tisch | Partisol | Tisch | Partisol | Tisch | Partisol | Tisch | Partisol | Tisch |
| | 0.349 | 0.391 | 1.650 | 1.148 | 0.780 | 0.614 | 0.221 | 0.150 | 0.321 | 0.403 | 0.749 | 0.550 | 0.011 | 0.016 |
| | 0.192 | 0.236 | 0.104 | 0.536 | 0.130 | 0.328 | 0.050 | 0.095 | | 0.217 | 0.048 | 0.200 | 0.004 | 0.007 |
| | 0.864 | 0.732 | 0.924 | 0.788 | 0.529 | 0.978 | 0.151 | 0.172 | 0.376 | 0.335 | 0.497 | 0.756 | 0.012 | 0.022 |
| | 0.475 | 0.384 | 0.396 | 0.397 | 0.300 | 0.323 | 0.089 | 0.083 | 0.135 | 0.158 | 0.220 | 0.286 | | |
| | 0.654 | 0.591 | 0.546 | 0.525 | 0.325 | 0.293 | 0.117 | 0.106 | 0.165 | 0.194 | 0.344 | 0.310 | 0.006 | 0.007 |
| | 1.019 | 0.827 | 1.619 | 1.480 | 0.771 | 0.891 | 0.223 | 0.244 | 0.604 | 0.563 | 1.006 | 0.974 | 0.009 | 0.023 |
| | 0.654 | 0.449 | 0.496 | 0.450 | 0.353 | 0.353 | 0.106 | 0.088 | 0.154 | 0.107 | 0.256 | 0.275 | 0.008 | 0.012 |
| | 0.615 | 0.477 | 1.003 | 0.696 | 0.545 | 0.678 | 0.170 | 0.186 | 0.347 | 0.202 | 0.577 | 0.818 | 0.006 | 0.018 |
| | 0.625 | 0.580 | 1.205 | 1.056 | 0.782 | 0.673 | 0.234 | 0.164 | 0.565 | 0.573 | 0.931 | 0.712 | | |
| | | | 1.751 | 1.789 | 1.052 | 0.938 | 0.263 | 0.239 | 0.672 | 0.829 | 0.945 | 0.844 | 0.019 | 0.026 |
| | | | 2.055 | 1.693 | 1.411 | 0.948 | 0.338 | 0.253 | 0.909 | 0.992 | 1.291 | 0.946 | 0.037 | 0.027 |
| | | | 0.906 | 0.665 | 0.461 | 0.786 | 0.109 | 0.133 | 0.327 | 0.270 | 0.473 | 0.666 | | |
| | | | 0.193 | 0.465 | 0.218 | 0.290 | 0.058 | 0.124 | 0.061 | 0.173 | 0.111 | 0.277 | | |
| | | | 2.176 | 2.334 | 1.464 | 1.166 | 0.314 | 0.275 | 0.851 | 0.984 | 1.437 | 1.254 | 0.028 | 0.026 |
| | | | 0.902 | 0.605 | 0.695 | 0.392 | 0.185 | 0.109 | 0.301 | 0.223 | 0.476 | 0.275 | 0.017 | 0.010 |
| Average Ratio | 0.86 | | 0.92 | | 0.98 | | 0.92 | | 1.00 | | 0.98 | | 1.23 | |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. An apparatus for sampling ambient air and removing particulate matter from the sampled ambient air as separate coarse and fine fractions:

a separating device connected to an upstream side of an acceleration tube for separating substantially all particulate matter larger than about 10 microns from ambient air and delivering ambient air containing the remaining coarse and fine fractions to a sample receiving end of said acceleration tube;

the acceleration tube extending along a central axis and comprising a conical section tapering from the sample receiving end down to an outlet straight cylinder section integral therewith, said outlet straight cylinder section having a constant diameter D1 and extending from said conical section to an outlet at a first distal end, wherein the sampled ambient air enters the sample receiving end of said acceleration tube at a first flow rate FR1;

a collection tube comprising an inlet straight cylinder section axially aligned with said acceleration tube, having a constant diameter D2, and extending along said central axis from an inlet at a second distal end to a conical section integral therewith, said conical section tapering from the diameter D2 to a discharge end of a diameter D3, larger than diameter D2, wherein the ratio of D2/D1 is >1 to 2 and wherein said first and second distal ends face each other and are spaced apart by a distance d, wherein the ratio of d/D1 is 1 to 2;

a housing surrounding at least the outlet straight cylinder section of said acceleration tube and the inlet straight cylinder section of said collection tube, said housing having a side-wall with a side-wall nozzle extending along a nozzle axis;

a fine particulate collector, for collecting the fine fraction, connected to said side-wall nozzle;

a large volume suction device connected to a downstream side of said fine particulate collector for drawing air at a second flow rate FR2 through said side-wall nozzle;

a coarse particulate collector, for collecting the coarse fraction, connected to the discharge end of said collection tube; and a small volume suction device connected to a downstream side of said coarse particular collector for drawing air at a third flow rate FR3, smaller than said second flow rate FR2, through said inlet of said collection tube.

2. An apparatus according to claim 1 wherein the ratio of D2/D1 is approximately 1.4 and the ratio of d/D1 is approximately 1.4.

3. An apparatus according to claim 1 wherein particulate matter in the air drawn through said side-wall nozzle is about 2.5 microns and smaller.

4. An apparatus according to claim 1 wherein said acceleration tube has an inlet straight cylinder section joined to said sample receiving end of said conical section at a first angle relative to said central axis and wherein said outlet straight cylinder section is joined to said conical section of said acceleration tube at a second angle relative to said central axis and wherein said first and second angles are 20-45°.

5. An apparatus according to claim 4 wherein said first and second angles are approximately 30°.

6. An apparatus according to claim 1 wherein said nozzle axis intersects said central axis at an angle of approximately 90°.

7. A method of using an apparatus according to claim 1, said method comprising:
   removing substantially all particulate matter larger than about 10 microns from ambient air;
   delivering ambient air containing the remaining coarse and fine fractions to the sample receiving end of said acceleration tube;
   introducing ambient air containing particulate matter in the remaining coarse and fine fractions into the sample receiving end of the acceleration tube at the first flow rate FR1;
   drawing a first portion of the introduced ambient air containing the fine fraction at the second flow rate FR2 through the side-wall nozzle;
   separating the fine fraction of particulate matter from the first portion of the introduced ambient air;
   drawing a second portion of the introduced ambient air containing the coarse fraction through the collection tube at a third flow rate FR3; and
   separating the coarse fraction of particulate matter from the second portion of the introduced ambient air.

8. A method according to claim 7 wherein the ratio of D2/D1 is approximately 1.4 and the ratio d/D1 is approximately 1.4.

9. A method according to claim 7 further comprising: adjusting at least one of the flow rates FR2 and FR3 to separate the fine and coarse fractions at a cut point of PM2.5.

10. A method according to claim 7 further comprising: adjusting at least one of the flow rates FR2 and FR3 to provide a ratio FR2/FR3 of 8:1 to 30:1.

11. A method according to claim 10 wherein the ratio FR2/FR3 is adjusted to approximately 25:1.

12. A method according to claim 7 further comprising: adjusting at least one of the flow rates FR2 and FR3 to provide a ratio FR2 to FR3 of 8:1 to 30:1.

13. A method according to claim 12 wherein the ratio FR2/FR3 is adjusted to approximately 25:1.

14. A method according to claim 7 wherein FR1 is 900-1200 liters/minute, FR2 is 800-1160 liters/minute and FR3 is 40-100 liters/minute, and wherein FR1 is equal to the sum of FR2 and FR3.

15. A method according to claim 9 wherein FR1 is 900-1200 liters/minute, FR2 is 800-1160 liters/minute and FR3 is 40-100 liters/minute, and wherein FR1 is equal to the sum of FR2 and FR3.

16. A method according to claim 1 wherein FR1 is 900-1200 liters/minute, FR2 is 800-1160 liters/minute and FR3 is 40-100 liters/minute, and wherein FR1 is equal to the sum of FR2 and FR3.

17. A method according to claim 10 wherein FR1 is 900-1200 liters/minute, FR2 is 800-1160 liters/minute and FR3 is 40-100 liters/minute, and wherein FR1 is equal to the sum of FR2 and FR3.

* * * * *